(12) United States Patent
Del Rio et al.

(10) Patent No.: US 10,961,314 B2
(45) Date of Patent: Mar. 30, 2021

(54) LIQUID PHARMACEUTICAL COMPOSITION COMPRISING AN ANTI-IL-6 RECEPTOR ANTIBODY

(71) Applicant: FRESENIUS KABI DEUTSCHLAND GMBH, Bad Homburg (DE)

(72) Inventors: Alessandra Del Rio, Rome (IT); Carmela Sabina, Tivoli (IT)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 16/334,310

(22) PCT Filed: Sep. 26, 2017

(86) PCT No.: PCT/EP2017/074413
§ 371 (c)(1),
(2) Date: Mar. 18, 2019

(87) PCT Pub. No.: WO2018/060210
PCT Pub. Date: Apr. 5, 2018

(65) Prior Publication Data
US 2019/0218300 A1    Jul. 18, 2019

(30) Foreign Application Priority Data
Sep. 27, 2016    (EP) .................................... 16190957

(51) Int. Cl.
| | | |
|---|---|---|
| *A61K 39/395* | (2006.01) | |
| *C07K 16/30* | (2006.01) | |
| *C07K 16/28* | (2006.01) | |
| *A61K 9/00* | (2006.01) | |
| *A61K 47/26* | (2006.01) | |
| *A61K 47/18* | (2017.01) | |
| *A61K 9/08* | (2006.01) | |
| *A61K 47/02* | (2006.01) | |
| *A61K 47/20* | (2006.01) | |
| *A61K 47/22* | (2006.01) | |

(52) U.S. Cl.
CPC ........ *C07K 16/2866* (2013.01); *A61K 9/0019* (2013.01); *A61K 9/08* (2013.01); *A61K 39/39591* (2013.01); *A61K 47/02* (2013.01); *A61K 47/183* (2013.01); *A61K 47/20* (2013.01); *A61K 47/22* (2013.01); *A61K 47/26* (2013.01); *C07K 2317/21* (2013.01); *C07K 2317/24* (2013.01); *C07K 2317/569* (2013.01); *C07K 2317/94* (2013.01)

(58) Field of Classification Search
None
See application file for complete search history.

(56) References Cited

FOREIGN PATENT DOCUMENTS

| | | | |
|---|---|---|---|
| WO | WO 2010/062896 A1 | 6/2010 | |
| WO | WO 2011/085158 A2 | 7/2011 | |
| WO | WO 2012/064627 A2 | 5/2012 | |
| WO | WO 2014/066468 A1 | 5/2014 | |

*Primary Examiner* — Christine J Saoud
*Assistant Examiner* — Jon M Lockard
(74) *Attorney, Agent, or Firm* — James S. Keddie; Bozicevic, Field & Francis LLP

(57) ABSTRACT

The present invention relates to a novel protein formulation. In particular, the invention relates to a liquid pharmaceutical composition of an antibody directed to Interleukin-6 receptor, a method of manufacturing the composition, a kit including the composition, a package including the composition and to methods of treatment using the composition and/or package.

12 Claims, 4 Drawing Sheets
Specification includes a Sequence Listing.

LIQUID PHARMACEUTICAL COMPOSITION COMPRISING AN ANTI-IL-6 RECEPTOR ANTIBODY

CROSS-REFERENCE TO RELATED APPLICATIONS

This application is a § 371 national phase of International Application No. PCT/EP2017/074413, filed on Sep. 26, 2017, which claims the benefit of European Application No. 16190957.7, filed on Sep. 27, 2016, which applications are incorporated by reference herein.

INTRODUCTION

The present invention relates to a novel protein formulation. In particular, the invention relates to a liquid pharmaceutical composition of an antibody directed to Interleukin-6 receptor, a method of manufacturing the composition, a kit including the composition, a package including the composition and to methods of treatment using the composition and/or package.

BACKGROUND

Several biologics have been approved since the 90's for treating autoimmune diseases, such as rheumatoid arthritis, juvenile arthritis and other autoimmune diseases. Among others, there are drugs targeting Tumor Necrosis Factor-α (such as Etanercept (marketed as Enbrel®), Adalimumab (marketed as Humira®) or Infliximab (marketed as Remicade®) as well as Interleukin-6 receptor (IL-6R)(such as tocilizumab (marketed as ROACTEMRA® or Actemra®)). Other drugs targeting IL-6R for the treatment of these disorders are under development or already in pre-registration before the health authorities, such as sapelizumab, vobarilizumab or sarilumab.

Tocilizumab for instance is generally delivered to a patient either via intravenous or subcutaneous injection, and is provided in a liquid form, typically in packages such as vials, prefilled syringes, or prefilled "pen devices". Current commercial formulations of tocilizumab comprise the following ingredients:

| Ingredients of the intravenous formulation | Ingredients of the subcutaneous formulation |
|---|---|
| Tocilizumab (20 mg/mL) | Tocilizumab (180 mg/mL) |
| disodium phosphate dodecahydrate | polysorbate 80 |
| sodium dihydrogen phosphate dehydrate | L-histidine and L-histidine monohydrochloride |
| polysorbate 80 | L-arginine and L-arginine hydrochloride |
| sucrose | L-methionine |
| water for injection | water for injection |
| pH of about 6.5 | pH of about 6.0 |

These formulations have been described respectively in PCT applications WO03068260 and WO2009084659. Other formulations directed to anti-IL-6R antibodies have been described such as the ones in WO0213860, WO2011085158 or yet WO2013063510.

When preparing a pharmaceutical composition comprising a bioactive protein, such as an antibody, said composition must be formulated in such a way that the activity of the protein is maintained for an appropriate period of time. A loss in activity/stability of the protein may result from chemical or physical instabilities of the protein notably due to denaturation, aggregation or oxidation. The resulting products may thus be pharmaceutically unacceptable, especially after storage for a long time. Although the use of excipient(s) is known to increase the stability of a given protein, the stabilizing effects of these excipients is highly dependent of the nature of the excipients and of the bioactive protein itself.

As underlined with tocilizumab, generally the antibodies are formulated with different excipients when they are market with different strengths (e.g. 20 mg/mL versus 180 mg/mL) or with different presentations (intravenous versus subcutaneous).

There remains a need for further formulations containing anti-IL-6R antibodies such as tocilizumab sapelizumab, vobarilizumab or sarilumab, as an active ingredient, wherein said formulations are stable for an appropriate period of time and suitable for use in injection, preferably for any type of injection. Said formulations could be useful for administration in the treatment of autoimmune diseases, such as rheumatoid arthritis and juvenile idiopathic arthritis. Even if the overall performance of the commercial formulations cannot be surpassed, an alternative formulation having comparative performance but being useful whatever the concentration of the antibody or whatever its presentation would represent a highly desirable replacement for the commercial formulations. Desirably, the problem(s) of the prior art may be solved whilst reducing the complexity of the formulation(s).

SUMMARY OF THE INVENTION

According to a first aspect of the present invention there is provided a liquid pharmaceutical composition comprising an antibody directed to interleukin-6 receptor (IL-6R) (such as tocilizumab, sapelizumab, vobarilizumab or sarilumab), a histidine buffer and a polyol (such as a sugar alcohol). Said composition further comprises a free amino acid, a surfactant and optionally a salt. Said composition is (substantially or entirely) free of arginine (suitably L-arginine).

According to a second aspect of the present invention there is provided a method of manufacturing a liquid pharmaceutical composition, the method comprising mixing together an antibody against IL-6R (such as tocilizumab, sapelizumab, vobarilizumab or sarilumab), an histidine buffer, a polyol (such as a sugar alcohol), a free amino acid, a surfactant and optionally a salt. Also provided is a liquid pharmaceutical composition obtainable by, obtained by, or directly obtained by a method of manufacturing a liquid pharmaceutical composition as defined herein.

According to a third aspect of the present invention there is provided a drug delivery device (e.g. pre-filled syringe or pen, or intravenous bag) comprising a liquid pharmaceutical composition as defined herein.

According to a fourth aspect of the present invention there is provided a kit of parts comprising a drug delivery device, a liquid pharmaceutical composition as defined herein (optionally contained in a package or container), and optionally a set of instructions with directions regarding the administration (e.g. intravenous or subcutaneous) of the liquid pharmaceutical composition.

In a fifth aspect of the present invention there is provided a package (e.g. pre-filled syringe, pen, intravenous bag, or a package/container containing any of the aforementioned) comprising a liquid pharmaceutical composition as defined herein.

According to a sixth aspect of the present invention there is provided a method of manufacturing a package or a drug delivery device, the method comprising incorporating a liquid pharmaceutical composition as defined herein within a package or drug delivery device. Also provided is a package or a drug delivery device obtainable by, obtained by, or directly obtained by a method of manufacturing a package or a drug delivery device as defined herein.

According to a seventh aspect of the present invention there is provided a liquid pharmaceutical composition as defined herein for use in therapy.

DEFINITIONS

Figure 1:
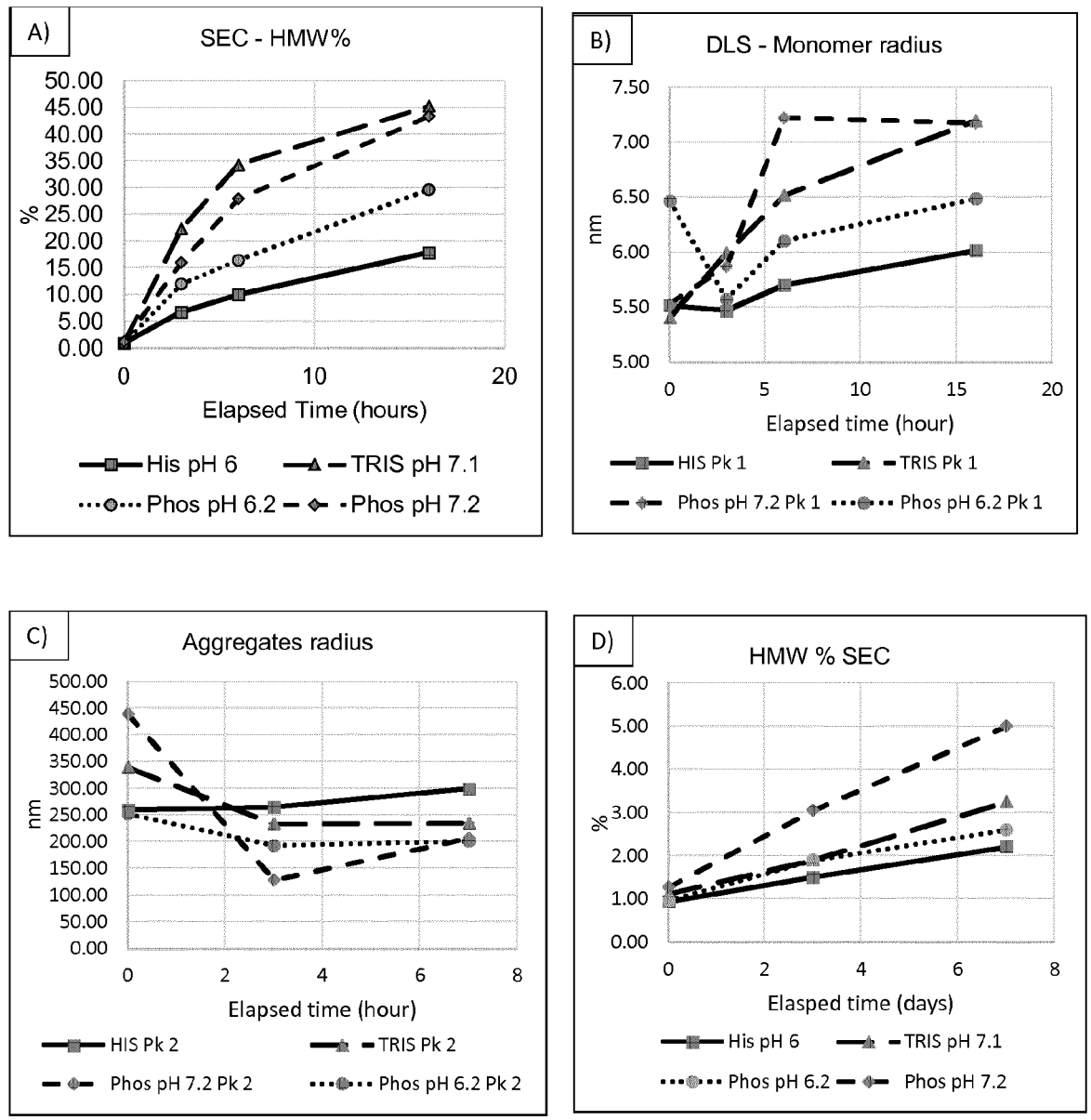
FIG. 1: buffer selection step. A) Light stress, High Molecular Weight (HMW) %, SEC data; B) Light stress, DLS (monomer radius), C) Thermal stress at 50° C., aggregates radius; D) Thermal stress at 50° C., HMW %, SEC data.

Any features, including optional, suitable, and preferred features, described in relation to any particular aspect of the invention may also be features, including optional, suitable and preferred features, of any other aspect of the present invention.

Unless otherwise stated, the following terms used in the specification and claims have the following meanings set out below.

The term "antibody", and its plural form "antibodies", as used herein includes, inter alia, polyclonal antibodies, affinity-purified polyclonal antibodies, monoclonal antibodies, and antigen-binding fragments, such as nanobodies, F(ab')2, Fab proteolytic fragments, and single chain variable region fragments (scFvs). It refers both to one-armed (monovalent) or two-armed (bivalent) antibody. The term "recombinant antibody" is intended to include an antibody prepared, expressed, produced or isolated using a recombinant method.

The term "anti-IL-6R antibody" refers to an antibody directed to interleukin-6 receptor (i.e. IL-6R). Preferably, it is an antibody which does not only bind to its target, i.e. the IL-6R, but also neutralise it (alternatively inhibit it or antagonise it).

The term "tocilizumab" includes the originator drug substance (as commercially available), as defined in WO9219759 (particularly hPM-1 therein) and elsewhere in the art, and also biosimilars thereof. Tocilizumab has a light chain variable region (LCVR) comprising the amino acid sequence of SEQ ID NO: 1 and a heavy chain variable region (HCVR) comprising the amino acid sequence of SEQ ID NO: 2. It has a molecular weight of about 145 kDa.

The term "sapelizumab" refers to an anti-IL6R antibody currently under development also known as SA-237, as well as biosimilars thereof. Sapelizumab has a light chain variable region (LCVR) comprising the amino acid sequence of SEQ ID NO: 3 and a heavy chain variable region (HCVR) comprising the amino acid sequence of SEQ ID NO: 4.

The term "vobarilizumab" refers to an anti-IL6R nanobody linked to an anti-human serum albumin nanobody, currently under development also named ALX-0061, as well as biosimilars thereof. Vobarilizumab comprises an amino acid sequence as defined in SEQ ID NO: 5. It has a molecular weight of about 257 kDa.

The term "sarilumab" refers to an anti-IL6R antibody currently in pre-registration before health authorities also named REGN-88 or SAR-153191, as well as biosimilars thereof. Sarilumab has a light chain variable region (LCVR) comprising the amino acid sequence of SEQ ID NO: 6 and a heavy chain variable region (HCVR) comprising the amino acid sequence of SEQ ID NO: 7. It has a molecular weight of about 144 kDa.

The term "biosimilar" refers to a drug substance which share full protein sequence identity with any one of drug substances on the market (i.e. approved by health Authorities). It is noted that a biosimilar may have a (slightly) different glycosylation profile. Such "biosimilars" would need to be officially approved as a "biosimilar" for marketing before said "biosimilar" is sold on the market. Herein, the term "buffer" or "buffer solution" refers to solutions of compounds that are known to be safe in formulations for pharmaceutical or veterinary use and that have the effect of maintaining or controlling the pH of the formulation in the pH range desired for the formulation. Acceptable buffers for controlling pH at a moderately acidic pH to a moderately basic pH include, but are not limited to, phosphate, acetate, lactate, citrate, arginine, TRIS, and histidine, salts and/or acidic forms thereof, and/or any combination thereof. "TRIS" refers to 2-amino-2-hydroxymethyl-1,3,-propane-diol, and to any pharmacologically acceptable salt thereof. The compound(s) making the buffer are also called "buffering agent(s)". According to the present invention, preferable buffers are histidine buffers. The pH of a "buffer solution" will change only slightly upon addition of a small quantity of strong acid or base due to the "buffering effect" imparted by the "buffering agent". It is noted that, a given concentration of a histidine buffer generally relates to the combined concentration of histidine and the imidazolium form (or protonated histidine salt) of histidine. However, in the case of histidine, such concentrations are usually straightforward to calculate by reference to the input quantities of histidine or a salt thereof. The overall pH of the composition is generally a reflection of the equilibrium concentration of each of the relevant buffering species (i.e. the balance of buffering agent(s) to acid/base conjugate(s) thereof).

Herein, the term "buffering agent" refers to an acid or base component (usually a weak acid or weak base) of a buffer or buffer solution. A buffering agent helps maintain the pH of a given solution at or near to a pre-determined value, and the buffering agents are generally chosen to complement the pre-determined value. A buffering agent is suitably a single compound which gives rise to a desired buffering effect, especially when said buffering agent is mixed with (and suitably capable of proton exchange with) an appropriate amount (depending on the pre-determined pH desired) of its corresponding "acid/base conjugate", or if the required amount of its corresponding "acid/base conjugate" is formed in situ—this may be achieved by adding strong acid or base until the required pH is reached.

Unless stated otherwise, references herein to an "amino acid" or "amino acids", whether specific (e.g. arginine, histidine) or general (e.g. any amino acid), in the context of their presence or otherwise within compositions (especially pharmaceutical liquid compositions of the invention) relate to the corresponding free amino acid(s) (regardless of its/their protonation state and/or salt form, though for consistency amounts are suitably calculated by reference to the free amino acid per se). This may suitably include natural and/or artificial amino acids. Unless stated to the contrary, such references are not intended to relate to amino acid residue(s) covalently incorporated as part of a larger compound (as opposed to a composition comprising multiple compounds), such as a peptide or protein (where such amino acid residues are linked via peptide bonds). As such, for example, though tocilizumab, as a protein, contains amino acid residues, it is not considered to comprise any "free amino acid(s)". By way of example, a composition defined as being "free of arginine" does not contain any free arginine but it may still include one or more proteins (e.g. tocilizumab) which do themselves comprise arginine residues. Unless stated otherwise, references herein to any one or more "amino acids", whether specific or general, suitably relate to the L-stereoisomers or a racemate thereof, most suitably L-amino acids.

The term "substantially free", when used in relation to a given component of a composition (e.g. "a liquid pharmaceutical composition substantially free of arginine"), refers to a composition to which essentially none of said component has been added. As explained above, such references have no bearing on the presence of amino acid residue(s) within a protein structure. When a composition is "substantially free" of a given component, said composition suitably comprises no more than 0.001 wt. % of said component, suitably no more than 0.0001 wt. % of said component, suitably no more than 0.00001 wt. %, suitably no more than 0.000001 wt. %, suitably no more than 0.0000001 wt. % thereof, most suitably no more than 0.0001 parts per billion (by weight).

The term "entirely free", when used in relation to a given component of a composition (e.g. "a liquid pharmaceutical composition substantially free of arginine"), refers to a composition containing none of said component. As explained above, such references have no bearing on the presence of amino acid residue(s) within a protein structure.

The term "stability", as used herein, refers to the physical, chemical, and conformational stability of tocilizumab in the formulations according to the present invention (and including maintenance of biological potency). Instability of a protein formulation may be caused by chemical degradation or aggregation of the protein molecules to form higher order polymers, deglycosylation, modification of glycosylation, oxidation or any other structural modification that reduces at least one biological activity of an antibody of the present invention.

The term "stable" solution or formulation, as used herein, is one solution or formulation wherein the degree of degradation, modification, aggregation, loss of biological activity and the like, of proteins therein is acceptably controlled, and does not increase unacceptably with time. It thus generally refers to the physical stability and/or chemical stability and/or biological stability of a component, typically an active or composition thereof, during preservation/storage.

Preferably, the formulation retains at least more than 80% of the antibody activity over a period of at least 12 months at room temperature and/or at lower temperatures (such as from 2 to 8° C.). The stabilized antibody formulation of the present invention has preferably a shelf-life of at least about 12 months, 18 months, more preferably at least 20 months, still more preferably about 24 months, when stored at room temperature, and/or at lower temperatures (such as from 2 to 8° C.). Methods for monitoring the stability of the antibody formulation of the present invention are available in the art, and include the methods described in the examples disclosed herein.

The term "stabilizing agent" or "stabilizer", as used herein, is a compound that is physiologically tolerated and imparts a suitable stability/tonicity to a formulation. It prevents notably the net flow of water across cell membranes that are in contact with the formulation. Compounds such as glycerin, are commonly used for such purposes. Other suitable stability agents include, but are not limited to, amino acids or proteins (e.g. glycine or albumin), salts (e.g. sodium chloride), and sugars (e.g. dextrose, mannitol, sucrose and lactose). According to the present invention, the preferred stabilizing agent is a polyol, even more preferably a sugar alcohol such as mannitol.

The term "surfactant", as used herein, refers to a soluble compound that can be used notably to increase the water solubility of hydrophobic, oily substances or otherwise increase the miscibility of two substances with different hydrophobicities. For this reason, these polymers are commonly used in industrial applications, cosmetics, and pharmaceuticals. They are also used as model systems for drug delivery applications, notably in order to modify the absorption of the drug or its delivery to the target tissues. Well known surfactants include polysorbates (polyoxyethylene derivatives; Tween) as well as poloxamers (i.e. copolymers based on ethylene oxide and propylene oxide, also known as Pluronics®). According to the invention, the preferred surfactant is a polysorbate surfactant and even more preferably is polysorbate 80.

The term "isotonicity agent" or "tonicifier", as used herein, is a compound that is physiologically tolerated and imparts a suitable tonicity to a formulation. It prevents notably the net flow of water across cell membranes that are in contact with the formulation. Compounds such as glycerin, are commonly used for such purposes. According to the present invention, the preferred isotonicity agent is a salt, even more preferably NaCl.

Herein, references to specific amounts of a given component of a composition, especially a buffering agent, suitably relate to the amounts of the pure anhydrous form of the relevant component (or compositions formed by using said amounts of the pure anhydrous form), even though such a component may be used in a non-anhydrous form when forming the composition. Amounts of any corresponding non-anhydrous forms (e.g. monohydrates, dihydrates, etc.) may be readily calculated by simply using the appropriate multiplier. For instance, unless stated otherwise (as per the Examples, where quantities relate to histidine), amounts stipulated in relation to histidine refer to the anhydrous form of histidine which has a molecular weight of about 155 g/mol. The skilled person would readily understand how to judiciously adjust the quantity of diluent/water depending on the form of the components used, in order to derive the target concentrations.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

Where a composition is said to comprise a plurality of ingredients (optionally in specific amounts of concentrations or in specific ranges of concentrations), said composition may optionally include additional ingredients other than those specifically mentioned.

DETAILED DESCRIPTION OF THE INVENTION

The main object of the present invention is a liquid pharmaceutical composition comprising an anti-IL-6R antibody, said antibody being able to neutralise (alternatively inhibit or antagonise) IL-6R activity. Preferably, the liquid pharmaceutical composition comprises an anti-IL-6R antibody such as tocilizumab, sapelizumab, vobarilizumab or sarilumab, including any biosimilar thereof. The composition preferably comprises a histidine buffer, keeping the pH in the range of 5.5 to 7.5, as well as a polyol. The composition is preferably (substantially or entirely) free of arginine. In addition, the composition may include any one or more additional components defined herein in relation to a liquid pharmaceutical composition (e.g. including tonicifier, surfactant, etc.), optionally in any amount, concentration, or form stipulated herein; and wherein the composition optionally exhibits any one or more parameters or properties given herein in relation to a liquid pharmaceutical composition (e.g. pH, osmolality). Preferably, the liquid pharmaceutical composition according to the invention comprises an anti-IL6-R antibody, a histidine buffer keeping the pH in the range of 5.5 to 7.5, a polyol, a polysorbate surfactant, a free amino acid and optionally a salt.

According to the present invention as a whole, the liquid pharmaceutical composition is (substantially or entirely) free of arginine (such as L-arginine).

The liquid pharmaceutical composition according to the present invention as a whole comprises the anti-IL-6R antibody at a concentration of or of about 10 to or to about 250 mg/ml, preferably of or of about 15 to or to about 200 mg/mL. For example, the anti-IL-6R antibody may be present in the formulation at a concentration of or of about 15, 20, 30, 40, 50, 60, 80, 100, 120,140, 160, 180 or 200 mg/ml. The anti-IL-6R antibody can be any known anti-IL6R antibody such as tocilizumab, sapelizumab, vobarilizumab or sarilumab (as defined herein).

Preferably the formulations of the invention retain at least 80% of the anti-IL-6R biological activity at the time of formulation and/or packaging over a period of at least 12 months (before the first use). Anti-IL-6R activity may be measured by any known methods.

The liquid pharmaceutical composition according to the present invention as a whole has a pH in the range of or of about 5.5 to or to about 7.5. Preferably, the liquid pharmaceutical composition has a pH in the range of or of about 6.0 to or to about 7.0. Suitably, the liquid pharmaceutical composition has a pH of or of about 6.0 or 6.5.

The buffer according to the present invention is a histidine buffer and is at a concentration of or of about 2 to or to about 50 mM. In an embodiment, the histidine buffer is present at a concentration of or of about 5 to or to about 30 mM, preferably at a concentration of or of about 10 to or to about 25 mM, even preferably at a concentration of or of about 20 mM.

Alternatively, the liquid pharmaceutical composition comprises the buffering species (suitably histidine buffering species—e.g. histidine itself) at a concentration of or of about 0.1 to or to about 10 mg/mL. In an embodiment, the buffering species is present at a concentration of or of about 0.5 to or to about 5 mg/mL, more preferably of or of about 2 to or to about 4 mg/mL. For example, the buffering species may be present in the formulation at a concentration of or of about 2.0 2.25, 2.5, 2.75, 3.0, 3.25, 3.5, 3.75 or 4.0 mg/mL. In an embodiment, the buffer system/buffering agent is present at a concentration of or of about 3.10 mg/mL.

Alternatively, the liquid pharmaceutical composition comprises the buffer in a molar ratio of buffer to anti-IL6R antibody of about 5:1 to about 200:1, and will mainly depend on the concentration of antibody in the formulation. For instance, when the anti-IL6R antibody is tocilizumab or sarilumab at 20 mg/mL the molar ratio is most suitably about 145:1 and when the anti-IL6R antibody is tocilizumab or sarilumab at 180 mg/mL the molar ratio is most suitably about 16:1.

The liquid pharmaceutical composition according to the invention as a whole comprises a stabiliser, most preferably a polyol. Suitably, such a component facilitates maintenance of the structural integrity of the biopharmaceutical drug, particularly during freezing and/or lyophilisation (if needed) and/or storage. The liquid pharmaceutical composition may comprise one or more polyols. Preferably, the polyol is a sugar polyol, such as a sugar alcohol. Even preferably, the sugar alcohol is selected from the group consisting of mannitol, sorbitol, xylitol, arabitol, erythritol, lactitol, maltitol or inositol. More preferably, the polyol (e.g. the sugar alcohol) is mannitol. Mannitol was indeed identified by the inventors as a particularly advantageous polyol stabiliser for use together with a histidine buffer in liquid anti-IL-6R antibody formulations.

The liquid pharmaceutical composition comprises the polyol(s) (such as mannitol) at a concentration of or of about 50 to or to about 400 mM, preferably from or from about 100 to or to about 300 mM, more preferably from or from of about 150 to or to about 250 mM. In an embodiment, the polyol(s) is/are present at a concentration of between 190 and 210 mM, most preferably at or at about 200 mM. In a particular embodiment, the polyol is mannitol and is present in the liquid pharmaceutical composition at a concentration of or of about 200 mM.

Alternatively, the liquid pharmaceutical composition comprises the polyol(s) (such as mannitol) at a concentration of or of about 1 mg/mL to or to about 100 mg/mL, more preferably of or of about 10 mg/mL to or to about 75 mg/mL, even more preferably of or of about 25 mg/mL to or to about 50 mg/mL. In an embodiment, the polyol(s) is/are present at a concentration of between 30 mg/mL and 40 mg/mL, most suitably about 36 mg/mL. For example, the polyol(s) (such as mannitol) may be present in the formulation at a concentration of or of about 25, 27.5, 30, 31, 32, 33, 34, 35, 36, 37, 38, 39, 40, 42.5, 45, 47.5 or 50 mg/mL In a particular embodiment, the polyol is mannitol and is present in the liquid pharmaceutical composition at a concentration of or of about 36 mg/mL.

Alternatively, the liquid pharmaceutical composition comprises the polyol(s) (such as mannitol) in a molar ratio of sugar stabilizer(s) to anti-IL-6R antibody of about 100:1 to about 1500:1, and will mainly depend on the concentration of antibody in the formulation. For instance, when the anti-IL6R antibody is tocilizumab or sarilumab at 20 mg/mL the molar ratio is most suitably about 1450:1 and when the anti-IL6R antibody is tocilizumab or sarilumab at 180 mg/mL the molar ratio is most suitably about 161:1.

The liquid pharmaceutical composition according to the present invention as a whole comprises at least one free amino acid other than histidine and arginine. Preferably, said free amino acid contains a sulphur element, such as cysteine or methionine. Even preferably, the free amino acid is methionine. Said component has been shown to be a good anti-oxidant.

The liquid pharmaceutical composition comprises the at least one free amino acid (such as methionine) at a concentration of or of about 0.1 to 5 mM, preferably of or of about 0.2 to or to about 2 mM, more preferably of or of about 0.4 to or to about 0.6 mM. For instance, the free amino acid(s) is/are present at a concentration of or of about 0.400, 0.425, 0.450, 0.475, 0.500, 0.550, 0.575 or 0.600 mM. In a particular embodiment, the at least one free amino acid is methionine and is present in the liquid pharmaceutical composition at a concentration of or of about 0.5 mM.

Alternatively, the liquid pharmaceutical composition comprises the at least one free amino acid (such as methionine) at a concentration of or of about 0.01 mg/mL to or to about 1 mg/mL, preferably of or of about 0.025 mg/mL to or to about 0.5 mg/mL, more preferably of or of about 0.05 mg/mL to or to about 0.2 mg/mL, even preferably of or of about 0.06 mg/mL to or to about 0.1 mg/mL. For instance, the at least one free amino acid(s) is/are present at a concentration of or of about 0.050, 0.055, 0.060, 0.065, 0.070, 0.075, 0.080, 0.085, 0.090, 0.095 or 0.1 mg/mL. In a particular embodiment, the at least one free amino acid is methionine and is present in the liquid pharmaceutical composition at a concentration of or of about 0.075 mg/mL.

Alternatively, the liquid pharmaceutical composition comprises the at least one amino acid (such as methionine) in a molar ratio of sugar stabilizer(s) to anti-IL-6R antibody of about 1:5 to about 5:1, and will mainly depend on the concentration of antibody in the formulation. For instance, when the anti-IL6R antibody is tocilizumab or sarilumab at 20 mg/mL the molar ratio is preferably about 36:10 and when the anti-IL6R antibody is tocilizumab or sarilumab at 180 mg/mL the molar ratio is most suitably about 2:5.

The liquid pharmaceutical composition according to the present invention as a whole contains surfactants. Preferred surfactants are polysorbates, such as polysorbate 20 (alternative name: polyoxyethylene (20) sorbitan monolaurate), polysorbate 40 (alternative name: polyoxyethylene (20) sorbitan monopalmitate), polysorbate 60 (alternative name: polyoxyethylene (20) sorbitan monostearate) or polysorbate 80 (alternative name: polyoxyethylene (20) sorbitan monooleate). Preferably the surfactant is polysorbate 80.

The liquid pharmaceutical composition comprises the surfactant, such as polysorbate 80, at a concentration of or of about 0.1 to or to about 5 mM, preferably from or from about 0.2 to or to about 2 mM, more preferably of or of about 0.4 to or to about 0.9 mM. For instance, the surfactant is present at a concentration of or of about 0.40, 0.45, 0.50, 0.55, 0.60, 0.65, 0.70, 0.75, 0.80, 0.85 or 0.90 mM. In a particular embodiment, the surfactant is polysorbate 80 and is present in the liquid pharmaceutical composition at a concentration of or of about 0.75 or 0.80 mM.

Alternatively, the liquid pharmaceutical composition comprises the surfactant, such as polysorbate 80, at a concentration of or of about 0.1 to or to about 10 mg/mL, preferably of or of about 0.25 to or to 5 mg/mL, more preferably of or of about 0.5 to or to about 2 mg/mL. For instance, the surfactant is present at a concentration of or of about 0.5, 0.6, 0.7, 0.8, 0.9, 1.0, 1.1, 1.2, 1.3, 1.4, 1.5, 1.75 or 2 mg/mL. In a particular embodiment, the surfactant is polysorbate 80 and is present in the liquid pharmaceutical composition at a concentration of or of about 1.0 mg/mL.

Alternatively, the liquid pharmaceutical composition comprises the surfactant (such as polysorbate 80) in a molar ratio of surfactant to anti-IL-6R antibody of about 1:2 to about 60:1, and will mainly depend on the concentration of antibody in the formulation. For instance, when the anti-IL6R antibody is tocilizumab or sarilumab at 20 mg/mL the molar ratio is preferably about 56:10 and when the anti-IL6R antibody is tocilizumab or sarilumab at 180 mg/mL the molar ratio is most suitably about 6:10.

The liquid pharmaceutical compositions of the invention may include any one or more pharmaceutically acceptable diluents, or mixture thereof. However, most suitably the liquid pharmaceutical composition is an aqueous pharmaceutical composition. Most suitably the diluent is water, and suitably water alone. The water is suitably water for injection (WFI). The diluent may constitute the balance of ingredients in any liquid pharmaceutical composition, for instance so that the weight percentages total 100%. Any concentrations given herein in relation to any component of the liquid pharmaceutical composition represent concentrations of said component in (and suitably dissolved in) the diluent in admixture with any other components.

The liquid pharmaceutical composition of the invention is suitably a solution, and is suitably (substantially or entirely) free of particulates or precipitates.

The liquid pharmaceutical composition according to the present invention as a whole may further comprise one or more excipients such as a salt. In a particular embodiment, there is at least one additional excipients which is a tonicifier. Preferably, if present, the tonicifier is or comprises sodium chloride (NaCl). Sodium chloride is a particularly advantageous stabiliser for use together with the histidine buffer in liquid anti-IL-6R antibody formulations.

Suitably, the liquid pharmaceutical composition comprises the salt (such as sodium chloride) at a concentration of or of about 20 to or to about 200 mM, preferably of or of about 50 to or to about 150 mM, more preferably of or of about 75 to or to about 125 mM. In an embodiment, the salt is present at a concentration of or of about 100 mM. In a particular embodiment, the salt is sodium chloride and is present at a concentration of or of about 100 mM. Alternatively, the liquid pharmaceutical composition comprises the salt (such as NaCl) at a concentration of or of about 0.5 mg/mL to or to about 25 mg/mL, preferably of or of about 1.0 mg/mL to or to about 10 mg/mL, more suitably of or of about 3 mg/mL to or to about 7 mg/mL. In an embodiment, the salt is present at a concentration of between 5 mg/mL and 6 mg/mL, most suitably about 5.84 mg/mL. In a particular embodiment, the salt is sodium chloride and is present at a concentration of about 5.84 mg/mL.

Alternatively, the liquid pharmaceutical composition comprises the salt (such as NaCl) in a molar ratio of salt to anti-IL-6R antibody of about 50:1 to about 800:1, and will mainly depend on the concentration of antibody in the formulation. For instance, when the anti-IL6R antibody is tocilizumab or sarilumab at 20 mg/mL the molar ratio is preferably about 725:1 and when the anti-IL6R antibody is tocilizumab or sarilumab at 180 mg/mL the molar ratio is most suitably about 80:1. In a further aspect, the present invention also provides a method of stabilising liquid anti-IL-6R antibody compositions, comprising mixing the anti-IL-6R antibody with any relevant components required to form a liquid pharmaceutical composition as defined herein. Therefore, herein provided is a method of manufacturing a liquid pharmaceutical composition, the method comprising mixing together an antibody against IL-6R, such as tocilizumab, an histidine buffer, a polyol (such as a sugar alcohol), and optionally any one or more additional components defined herein in relation to a liquid pharmaceutical composition, optionally in any amount, concentration, or form stipulated; and optionally adjusting any one or more parameters given herein in relation to a liquid pharmaceutical composition (e.g. pH, osmolality). Other relevant components can include at least one free amino acid (such as methionine), a surfactant (such as polysorbate 80) and optionally a salt (such as NaCl). Each of these compounds (i.e. anti-IL-6R antibody, the histidine buffer, the polyol, the surfactant, the at least one free amino acid, and/or the salt) can be used according to the concentrations, pH, and/or ratios herein described. If needed, the skilled person may refer to the Examples or techniques well known in the art for forming liquid pharmaceutical compositions (especially those for injection via syringe).

In an embodiment, the method involves mixing together the relevant components in a diluent (e.g. water), so that all of the components are (substantially or entirely) dissolved in the diluent. Also provided is a liquid pharmaceutical composition obtainable by, obtained by, or directly obtained by a method of manufacturing a liquid pharmaceutical composition as defined herein.

Suitably, the liquid pharmaceutical compositions of the invention have a shelf life of at least 6 months, suitably at least 12 months, suitably at least 18 months, more suitably at least 24 months. Suitably, the liquid pharmaceutical compositions of the invention have a shelf life of at least 6 months, suitably at least 12 months, suitably at least 18 months, more suitably at least 24 months, at a temperature of 2-8° C.

In certain embodiments, the buffering agent and/or the buffer is pre-formed as a separate mixture, and the buffer is transferred to a precursor of the liquid pharmaceutical composition (comprising some or all components except the buffer) via buffer exchange (e.g. using diafiltration until the relevant concentrations or osmolality is reached). Additional excipients may be added thereafter if necessary in order to produce the final liquid pharmaceutical composition. The pH may be adjusted once or before all the components are present.

The final liquid pharmaceutical composition may be filtered, suitably to remove particulate matter. Suitably filtration is through filters sized at or below 1 μm, suitably at 0.22 μm. For instance, filtration is mode through PES filters or PVDF filters at 0.22 μm.

In a third aspect, the present invention provides a drug delivery device comprising a liquid pharmaceutical composition as defined herein. Preferably the drug delivery device comprises a chamber within which the pharmaceutical composition resides. More preferably, the drug delivery device is sterile.

The drug delivery device may a vial, ampoule, syringe, injection pen (e.g. essentially incorporating a syringe), or intravenous bag. When the drug delivery device is a syringe, it is preferably an injection pen. Suitably the syringe is a glass syringe.

In a fourth aspect, the present invention provides a kit of parts comprising a drug delivery device (without the liquid pharmaceutical composition incorporated therein), a liquid pharmaceutical composition as defined herein (optionally contained in a separate package or container), and optionally a set of instructions with directions regarding the administration (e.g. sub-cutaneous or intravenous) of the liquid pharmaceutical composition. The user may then fill the drug delivery device with the liquid pharmaceutical composition (which may be provided in a vial or ampoule or such like) prior to administration.

Also described, as a fifth aspect, is a package comprising a liquid pharmaceutical composition as defined herein. Suitably the package comprises a drug delivery device as defined herein, suitably a plurality of drug delivery devices. The package may comprise any suitably container for containing one or more drug delivery devices.

The present invention provides, in a sixth aspect, a method of manufacturing a drug delivery device, suitably as defined herein, the method comprising incorporating a liquid pharmaceutical composition as defined herein within a drug delivery device. Such manufacture typically involves charging the liquid pharmaceutical composition as defined herein to a syringe, suitably via a needle affixed thereto. The needle may thereafter be removed, replaced, or remain. Also disclosed is a drug delivery device obtainable by, obtained by, or directly obtained by a method of manufacture defined herein.

Also described is a method of manufacturing a package, the method comprising incorporating a liquid pharmaceutical composition as defined herein within a package. Suitably this is achieved by incorporating said liquid pharmaceutical composition within one or more drug delivery devices, and thereafter incorporating the one or more pre-filled drug delivery devices into a container present within the package. The present invention provides, in addition, a package obtainable by, obtained by, or directly obtained by a method of manufacture defined herein.

The liquid pharmaceutical compositions defined herein may be used to treat any one or more of the aforementioned diseases or medical disorders. In a particular embodiment, the liquid pharmaceutical compositions are used to treat rheumatoid arthritis and juvenile idiopathic arthritis.

Alternatively, the liquid pharmaceutical compositions are used to treat other diseases such as giant cell arteritis or systemic sclerosis.

The liquid pharmaceutical compositions are suitably parenterally administered, either via intravenous injection or via sub-cutaneous injection.

PARTICULAR EMBODIMENTS

In an embodiment, the liquid pharmaceutical composition comprises:
An anti-IL-6R antibody (such as tocilizumab, sapelizumab, vobarilizumab or sarilumab);
histidine buffer keeping the pH between about 5.5 to 7.5;
a polyol (e.g. mannitol);
a free amino acid (e.g. methionine);
a surfactant (e.g. polysorbate 80);
water for injection; and
optionally a salt (e.g. NaCl).

In an embodiment, the liquid pharmaceutical composition comprises:
An anti-IL-6R antibody (such as tocilizumab, sapelizumab, vobarilizumab or sarilumab), wherein the antibody is at a concentration of 10 to 250 mg/mL;
histidine buffer keeping the pH between about 5.5 to 7.5;
a polyol (e.g. mannitol);
a free amino acid (e.g. methionine);
a surfactant (e.g. polysorbate 80);
water for injection; and
optionally a salt (e.g. NaCl).

In an embodiment, the liquid pharmaceutical composition comprises:
An anti-IL-6R antibody (such as tocilizumab, sapelizumab, vobarilizumab or sarilumab);
histidine buffer keeping the pH between about 5.5 to 7.5, wherein the buffer is at a concentration of 2 to 50 mM, or alternatively at a concentration of 0.1 to 10 mg/mL or alternatively at a molar ratio buffer to antibody of 5:1 to 200:1;
a polyol (e.g. mannitol);
a free amino acid (e.g. methionine);
a surfactant (e.g. polysorbate 80);
water for injection; and
optionally a salt (e.g. NaCl).

In an embodiment, the liquid pharmaceutical composition comprises:
An anti-IL-6R antibody (such as tocilizumab, sapelizumab, vobarilizumab or sarilumab);
histidine buffer keeping the pH between about 5.5 to 7.5;
a polyol (e.g. mannitol), wherein the polyol is at a concentration of 50 to 400 mM, or alternatively at a concentration of 1 to 100 mg/mL or alternatively at a molar ratio polyol to antibody of 100:1 to 1500:1;
a free amino acid (e.g. methionine);
a surfactant (e.g. polysorbate 80);
water for injection; and
optionally a salt (e.g. NaCl).

In an embodiment, the liquid pharmaceutical composition comprises:
An anti-IL-6R antibody (such as tocilizumab, sapelizumab, vobarilizumab or sarilumab);
histidine buffer keeping the pH between about 5.5 to 7.5;
a polyol (e.g. mannitol);
a free amino acid (e.g. methionine), wherein the free amino acid is at a concentration of 0.1 to 5 mM, or alternatively at a concentration of 0.01 to 1 mg/mL or alternatively at a molar ratio free amino acid to antibody of 1:5 to 5:1;
a surfactant (e.g. polysorbate 80);
water for injection; and
optionally a salt (e.g. NaCl).

In an embodiment, the liquid pharmaceutical composition comprises:
An anti-IL-6R antibody (such as tocilizumab, sapelizumab, vobarilizumab or sarilumab);
histidine buffer keeping the pH between about 5.5 to 7.5
a polyol (e.g. mannitol);
a free amino acid (e.g. methionine);
a surfactant (e.g. polysorbate 80), wherein the free amino acid is at a concentration of 0.1 to 5 mM, or alternatively at a concentration of 0.1 to 10 mg/mL or alternatively at a molar ratio surfactant to antibody of 1:2 to 60:1;
water for injection; and
optionally a salt (e.g. NaCl).

In an embodiment, the liquid pharmaceutical composition comprises:
An anti-IL-6R antibody (such as tocilizumab, sapelizumab, vobarilizumab or sarilumab);
histidine buffer keeping the pH between about 5.5 to 7.5
a polyol (e.g. mannitol);
a free amino acid (e.g. methionine);
a surfactant (e.g. polysorbate 80);
water for injection; and
optionally a salt (e.g. NaCl), wherein the free amino acid is at a concentration of 20 to 200 mM, or alternatively at a concentration of 0.5 to 25 mg/mL or alternatively at a molar ratio salt to antibody of 50:1 to 800:1.

In an embodiment, the liquid pharmaceutical composition comprises:
An anti-IL-6R antibody (such as tocilizumab, sapelizumab, vobarilizumab or sarilumab), wherein the antibody is at a concentration of 10 to 250 mg/mL;
histidine buffer keeping the pH between about 5.5 to 7.5; wherein the buffer is at a concentration of 2 to 50 mM, or alternatively at a concentration of 0.1 to 10 mg/mL or alternatively at a molar ratio buffer to antibody of 5:1 to 200:1;
a polyol (e.g. mannitol), wherein the polyol is at a concentration of 50 to 400 mM, or alternatively at a concentration of 1 to 100 mg/mL or alternatively at a molar ratio polyol to antibody of 100:1 to 1500:1;
a free amino acid (e.g. methionine), wherein the free amino acid is at a concentration of 0.1 to 5 mM, or alternatively at a concentration of 0.01 to 1 mg/mL or alternatively at a molar ratio free amino acid to antibody of 1:5 to 5:1;
a surfactant (e.g. polysorbate 80), wherein the free amino acid is at a concentration of 0.1 to 5 mM, or alternatively at a concentration of 0.1 to 10 mg/mL or alternatively at a molar ratio surfactant to antibody of 1:2 to 60:1;
water for injection; and
optionally a salt (e.g. NaCl), wherein the free amino acid is at a concentration of 20 to 200 mM, or alternatively at a concentration of 0.5 to 25 mg/mL or alternatively at a molar ratio salt to antibody of 50:1 to 800:1.

EXAMPLES

Materials and Equipment

The following materials were used in the preparation of formulations described in the Examples that follow:

| Ingredient | Supplier/reference |
| --- | --- |
| Tocilizumab | Toci-052-UF-DS (internal) |
| Glutathione-L reduced | G4251 |
| Histidine Chloride | 104354 (Merck) |
| Hydrochloridric acid 1N | 109057 (Merck) |
| Kollidon 12 PF | 50348141 (BASF) |
| Kolliphor ELP | 50259800 (BASF) |
| L-Arginine | 101587 (Merck) |
| L-Arginine hydrochloride | 101544 (Merck) |
| L-Histidine | 1.04352 (Merck) |
| L-Histidine monohydrochloride | 1.04354 (Merck) |
| L-methionine | 95811601CM (Evonik Rexim) |
| Mannitol | 1.05303 (Merck) |
| Polysorbate 80 | 8.17061 (Merck) |
| Sodium Chloride | 1.16224 (Merck) |
| Sodium Citrate | 1613859 (Merck) |
| Sodium hydroxide | 106498 (Merck) |
| Sodium Phosphate dibasic | 106576 (Merck) |
| Thioglicerol-1 | 56454 (Sigma) |
| Tris (hydroxymethyl)aminomethane hydrochloride | 108219 (Merck) |
| WFI | 3033965 (Eurospital) |

The following disposable equipment and materials were used in the Examples and Screen Experiments which follow.

| Item | Code | Supplier |
|---|---|---|
| Eppendorf Tubes (0.5 mL, 1.5 mL, 2.0 mL) | NA | Eppendorf |
| Falcon (polypropylene tubes) | 352096 (15 mL), 352070 (50 mL) | Becton Dickinson |
| PES membrane (0.22 μm) filter unit | MillexGP Express PES membrane REF SLGP033RS | Millipore |
| PETG bottles | 3420-1000, 3420-0500, 2019-0250, 3420-0125, 3420-0060, 2019-0030 | Nalgene |
| DIN2R Type I glass vials | NA | Schott |
| Bromobutyl rubber stoppers | 4023/50 gray FluroTec | West Pharmaceuticals |

The following equipment was used in the Examples and Screen Experiments which follow.

| Item | Mod. | Manufacturer |
|---|---|---|
| HPLC systems | Alliance | Waters |
| DLS/SLS | Z-sizer Nano | Alfatech |
| UV Spectrophotometer | Lambda 35 | Perkin Elmer |
| Analytical scales | AX204 | Mettler Toledo |
| pH - meter | Seven Multi | Mettler Toledo |
| Density Meter | DE45 Delta Range | Mettler Toledo |
| DSF | AB 7500 RT Fast | Applied Biosystem |
| Fluorimeter | Fluoromax 3 | Horiba |
| Rheometer | Discover HR3 | TA instrument |
| Osmometer | Osmomat 030-D | Gonotec |
| Calibrated Pipettes | P100, P200, P1000 | Gilson |
| 96 wells PCR plates | Micro AMP plate | AB |

Analytical Techniques and Protocols

The following analytical methods of protocols were employed, in the Examples and Screening Experiments which follow, for the reasons stated in the table below:

| Analytical Method | Scope of the test |
|---|---|
| OD | Protein content |
| SE-HPLC | Aggregation |
| CEX-HPLC | Isoforms distribution |
| Potentiometric | pH |
| Rheometry | Viscosity |
| Osmometry | Osmolality |
| Dynamic Light Scattering (DLS) | Aggregation |
| Differential Scanning Fluorimetry (DSF) | Melting temperature |
| CE-SDS (non reducing conditions) | Fragmentation |

The individual protocols for each of the above analytical methods are described in turn below, and references in the Examples and Screening Experiments to any such analytical methods used these protocols.

1. Thermal Stress

Each sample was incubated at 50° C.; at each time point the required amount of sample was withdrawn and immediately analysed or stored at −80° C. before testing.

2. Mechanical Stress

Each sample of 5 ml volume was put in a 10 ml Nalgene squared bottle and subjected to orbital shaking (150 rpm; room temperature) up to 14 days. At each time point the relevant containers was withdrawn to be either tested immediately or stored at −80° C. before testing.

3. Light Stress

Exposure was conducted at 765 Wh/m2. The samples exposed to irradiation were placed alongside with required amount of control samples (to be kept in the same chamber but without being irradiated). After exposure, at each time point, the required amount of samples was withdrawn to be tested immediately or stored at −80° C. before testing.

4. Oxidation Stress

Each sample (100 μL) was added with 100 μL of H2O2 2% v/v to get the final concentration of 1%. The solution was incubated at 25° C. In case the solution becomes cloudy, the plate was spin down at 10000 g for 25 min at RT ° C.

5. Other Methods

Standard methods were used for:
Visible particles,
Protein content,
SE-HPLC,
CE-SDS,
CEX-HPLC
pH,
Osmolality (Time 0, only).

The study aimed to develop one new liquid formulation of anti-IL-6R antibody, for both subcutaneous and/or intravenous use. The formulation development was composed of the following phases:

1. Buffers selection (DS DoE).
2. Excipients selection (DP DoE).

Formal stability studies were performed as follow (Table 1):

| | Temperature (° C.) | Residual humidity (%) |
|---|---|---|
| DS | −80 ± 10 | N/A |
| | −20 ± 5 | |
| | 5 ± 3 | |
| DP | 40 ± 2 | 75 ± 5 |
| | 25 ± 2 | 60 ± 5 |
| | 5 ± 3 | N/A |

Example 1—Screening of the Buffers

DS buffer screen was executed using a DoE approach. From an initial high number of buffers, through a combined approach of thermodynamic and kinetic parameters a final buffer was selected, as well as one back up. The anti-IL-6R antibody that was used in this example is tocilizumab.

After purification, the antibody was exchanged by centrifugation with 4 different buffers:
Phosphate buffer pKa=7.2,
Phosphate Citrate buffer pKa=6.40,
TRIS buffer pKa=8.1,
Histidine pKa=6.0.

The DS was composed only of the mAb and the buffer, the aim of this step was to evaluate the single interaction of the two components. The experimental matrix was as followed (see Table 2 below):

| Buffer system | Sample n° | Concentration | pH |
|---|---|---|---|
| Phosphate | 1 | 10 | 6.2 |
| | 2 | 10 | 8.2 |
| | 3 | 20 | 7.2 |
| | 4 | 30 | 6.2 |
| | 5 | 30 | 8.2 |
| Phosphate | 6 | 10 | 5.4 |

| Buffer system | Sample n° | Concentration | pH |
|---|---|---|---|
| Citrate | 7 | 10 | 7.4 |
|  | 8 | 20 | 6.4 |
|  | 9 | 30 | 5.4 |
|  | 10 | 30 | 7.4 |
| TRIS | 11 | 10 | 7.1 |
|  | 12 | 10 | 9.1 |
|  | 13 | 20 | 8.1 |
|  | 14 | 30 | 7.1 |
|  | 15 | 30 | 8.1 |
| Histidine | 16 | 20 | 6.0 |

Exchange by concentration and concentration are well within the knowledge of the skilled person, and therefore are not herein detailed. The antibody target concentration was above 210 mg/mL. The Differential Scanning Fluorimetry (DSF) technology (*High throughput thermostability screening of monoclonal antibody formulations. J Pharm Sci.* 2010 April; 99(4):1707-20) with SyproOrange dye was used to preselect the buffers. Stress tests phase was run with the buffers having the higher Th and the lower aggregation percentage, as per DSF:

Histidine 20 mM, pH 6.0,
TRIS 20 mM pH 6.2,
Phosphate 20 mM pH 6.2,
Phosphate 20 mM pH 7.2.

Stress tests used were:
Thermal stress,
Mechanical stress,
Light stress,
Oxidation.

Light Stress:
FIGS. 1A and 1B show the results respectively on high molecular weight species (HMW) and on monomer radius. Histidine buffer, 20 mM, at pH 6.0 as well as phosphate buffer, 20 mM, at pH 6.2, presented the lowest increase of HMW %, as well as the lowest increase of monomer radius. It is noted that TRIS buffer gave slightly more protection against light stress than phosphate buffer.

Thermal Stress:
FIGS. 1C and 1B show the results respectively on aggregates radius and high molecular weight species (HMW). Very low increase of aggregate radius was observed for all the samples except for phosphate pH 7.2. Histidine buffer, 20 mM, at pH 6.0 as well as phosphate buffer, 20 mM, at pH 6.2, presented the lowest increase of HMW. Most aggregated samples were the ones with phosphate buffer pH 7.2.

Figure 2:
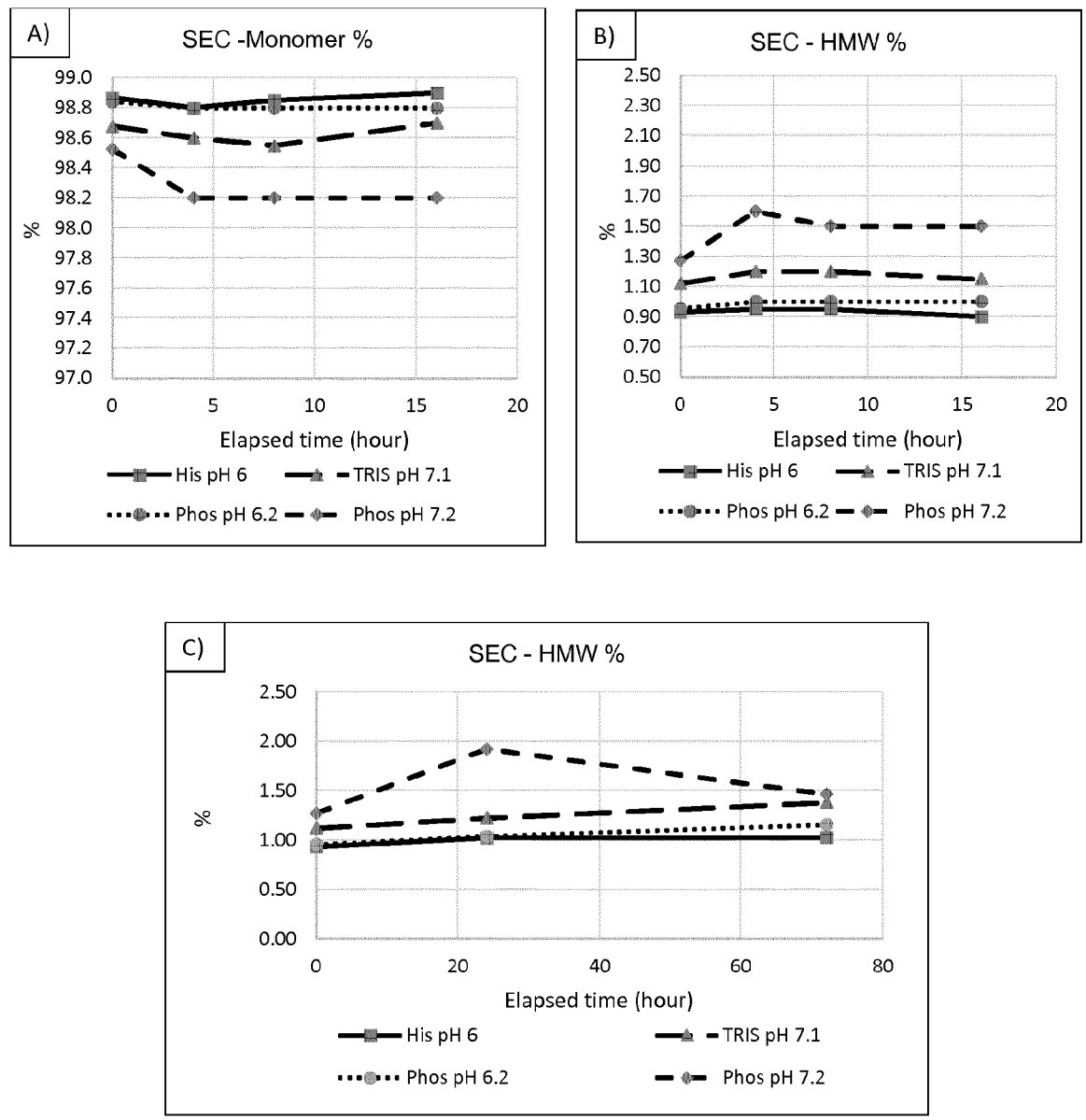
FIG. 2: buffer selection step. A) Oxidation stress, Monomer %, SEC data; B) Oxidation stress, High molecular weight %, SEC data; C) Mechanical stress, High molecular weight %, SEC data.

Oxidation Stress:
FIGS. 2A and 2B show the results respectively on monomer % and high molecular weight species (HMW). Very low HMW increase of aggregate radius was observed for all the samples.

Mechanical Stress:
FIG. 2C shows the results on high molecular weight species (HMW). The lowest increase of HMW % was observed for phosphate buffer, pH 6.2 and for Histidine buffer, pH 6.0.

Viscosity:
The data underlined that phosphate buffers had a higher viscosity than either histidine or TRIS buffer (see table 3 below)

| | Viscosity (mPa · S) | | |
|---|---|---|---|
| SAMPLE TESTED | 5° C. | 20° C. | 25° C. |
| Phos pH 7.2 | 256 | 89 | 80 |
| Phos pH 6.2 | 226 | 66 | 35 |
| TRIS pH 7.1 | 73 | 28 | 24 |
| His pH 6.0 | 72 | 31 | 29 |

CONCLUSION

Based on the results of the buffers screening, the selected buffers were: Histidine buffer, 20 mM, at pH 6.0 (as the lead buffer) as well as TRIS buffer, 20 mM, at pH 7.1 (as the back-up).

Example 2—Screening of the Excipients

The aim was to develop formulations made of five components: buffer, antioxidant, surfactant, tonicity and stabilizing agent. The same approach used for the buffer selection was applied to the excipients screening: 1) High throughput excipients screening by SE-HPLC (about 40 different formulations), 2) stress tests on the selected formulations, 3) selection of one lead formulation and one (or two) back-ups. The formulations stability will then by tested for several months. The experimental matrix for the DoE is reported in Table 4:

Osmolality was adjusted with an isotonicity agent (Sodium Chloride to adjust the osmolality to 300 mOsm/Kg).

The selected formulations were stressed with the same conditions described for the buffer selection. From the stress tests, the resulting 1 lead formulation (TOM 4) was selected and put in stability for several months in the final primary container.

Figure 3:
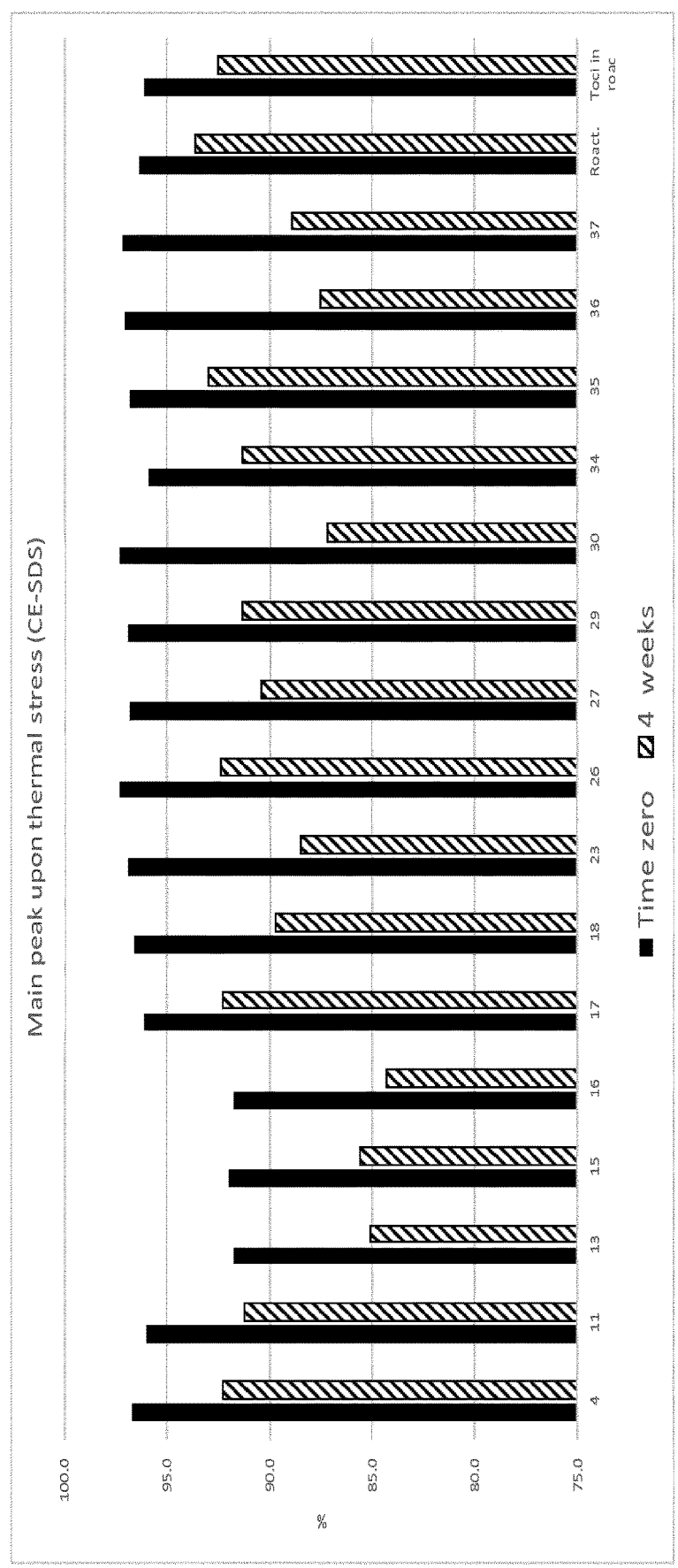
FIG. 3: behaviour of the formulations under thermal stress—results on main peak variations (CE-SDS).

Thermal Stress:
FIG. 3 shows the results on main peak variations (CE-SDS). Formulations TOM 4, TOM 11, TOM 17, TOM 29, TOM 34 and TOM 35 presented the lowest variation compared to RoActemra. They are all formulated in histidine 20 mM.

Figure 4:
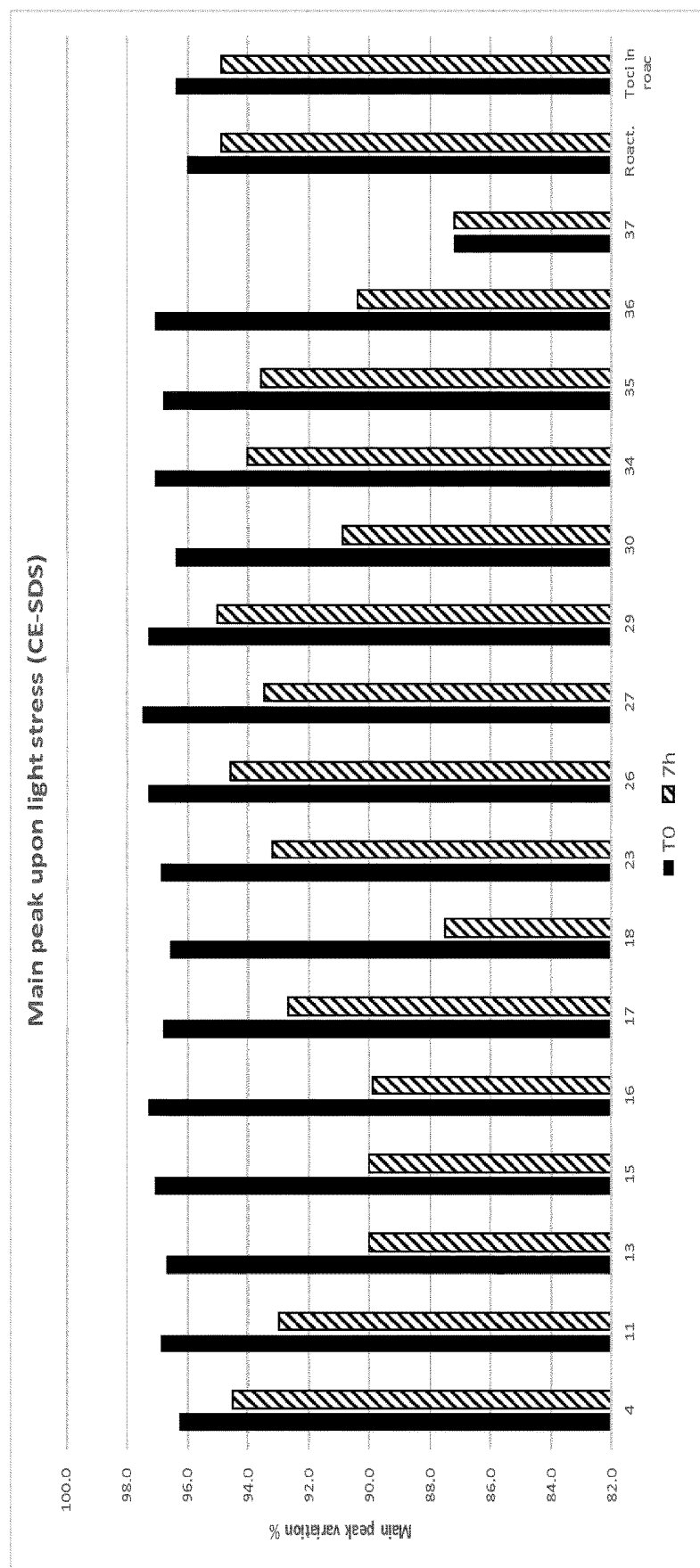
FIG. 4: behaviour of the formulations under light stress—results on main peak variations (CE-SDS).

Light Stress:
FIG. 4 shows the results on main peak variations (CE-SDS). Formulations TOM 4, TOM 26, TOM 27, TOM 29, TOM 34, TOM 35 presented the lowest variation compared to RoActemra. They are all formulated in histidine 20 mM.

TABLE 4 experimental matrix for the DoE of example 2. When arginine is mentioned in this table as a bulking agent, it is to be understood as arginine monohydrate; TRIS, in the buffer column, refers to TRIS 20 mM pH 7.1 and histidine, in the buffer column, refers to Histidine 20 mM pH 6.0.

| # of Formulation | Bulking agent | Bulking agent (mM) | NaCl Conc (mM) | Surfactant | Surfactant (mg/ml) | Antioxidant | Antioxidant conc (mg/ml) | BUFFER | Calculated Osmolality (mOsm/Kg) |
|---|---|---|---|---|---|---|---|---|---|
| TOM 1 | Mannitol | 200 | 25 | Kolliphor ELP | 0.1 | L-Methionine | 0.75 | TRIS | 290 |
| TOM 2 | Mannitol | 50 | 100 | Tween 80 | 0.1 | L-Methionine | 0.75 | TRIS | 290 |

TABLE 4-continued experimental matrix for the DoE of example 2. When arginine is mentioned in this table as a bulking agent, it is to be understood as arginine monohydrate; TRIS, in the buffer column, refers to TRIS 20 mM pH 7.1 and histidine, in the buffer column, refers to Histidine 20 mM pH 6.0.

| # of Formulation | Bulking agent | Bulking agent (mM) | NaCl Conc (mM) | Surfactant | Surfactant (mg/ml) | Antioxidant | Antioxidant conc (mg/ml) | BUFFER | Calculated Osmolality (mOsm/Kg) |
|---|---|---|---|---|---|---|---|---|---|
| TOM 3 | Mannitol | 200 | 25 | Kolliphor ELP | 1 | L-Methionine | 0.075 | TRIS | 290 |
| TOM 4 | Mannitol | 200 | 100 | Tween 80 | 1 | L-Methionine | 0.075 | Histidine | 420 |
| TOM 5 | Mannitol | 200 | 100 | Tween 80 | 1 | L-Methionine | 0.75 | TRIS | 440 |
| TOM 6 | Arginine | 50 | 25 | Kolliphor ELP | 0.1 | L-Methionine | 0.075 | TRIS | 190 |
| TOM 7 | Mannitol | 200 | 100 | Kollidon 12PF | 0.1 | L-Methionine | 0.075 | TRIS | 440 |
| TOM 8 | Mannitol | 50 | 100 | Kollidon 12PF | 0.1 | L-Methionine | 0.75 | TRIS | 290 |
| TOM 9 | Mannitol | 200 | 100 | Tween 80 | 0.1 | L-Methionine | 0.75 | TRIS | 440 |
| TOM 10 | Mannitol | 50 | 100 | Kollidon 12PF | 0.1 | L-Methionine | 0.075 | TRIS | 290 |
| TOM 11 | Mannitol | 50 | 100 | Kolliphor ELP | 1 | Thioglycerol | 0.075 | Histidine | 270 |
| TOM 12 | Mannitol | 50 | 25 | Tween 80 | 0.1 | Thioglycerol | 0.075 | TRIS | 140 |
| TOM 13 | Arginine | 200 | 25 | Tween 80 | 0.1 | Thioglycerol | 0.75 | Histidine | 470 |
| TOM 14 | Arginine | 50 | 25 | Tween 80 | 0.1 | Thioglycerol | 0.75 | TRIS | 190 |
| TOM 15 | Mannitol | 50 | 25 | Kollidon 12PF | 0.1 | Thioglycerol | 0.75 | Histidine | 120 |
| TOM 16 | Arginine | 200 | 100 | Kollidon 12PF | 1 | Thioglycerol | 0.075 | Histidine | 620 |
| TOM 17 | Mannitol | 200 | 100 | Kolliphor ELP | 0.1 | Thioglycerol | 0.75 | Histidine | 420 |
| TOM 18 | Arginine | 50 | 25 | Tween 80 | 1 | Thioglycerol | 0.075 | Histidine | 170 |
| TOM 19 | Arginine | 200 | 100 | Tween 80 | 0.1 | Thioglycerol | 0.075 | TRIS | 640 |
| TOM 21 | Arginine | 50 | 100 | Kolliphor ELP | 1 | Thioglycerol | 0.075 | TRIS | 340 |
| TOM 22 | Arginine | 200 | 100 | Kollidon 12PF | 0.1 | Thioglycerol | 0.75 | TRIS | 640 |
| TOM 23 | Arginine | 50 | 100 | Kollidon 12PF | 1 | Thioglycerol | 0.75 | Histidine | 320 |
| TOM 24 | Arginine | 200 | 25 | Kolliphor ELP | 0.1 | Thioglycerol | 0.075 | TRIS | 490 |
| TOM 25 | Mannitol | 200 | 25 | Kollidon 12PF | 1 | Thioglycerol | 0.075 | TRIS | 290 |
| TOM 26 | Mannitol | 200 | 25 | Kolliphor ELP | 1 | Glutathione | 0.75 | Histidine | 270 |
| TOM 27 | Mannitol | 200 | 25 | Kolliphor ELP | 0.1 | Glutathione | 0.075 | Histidine | 270 |
| TOM 28 | Arginine | 200 | 25 | Tween 80 | 1 | Glutathione | 0.075 | TRIS | 490 |
| TOM 29 | Arginine | 200 | 25 | Kollidon 12PF | 0.1 | Glutathione | 0.75 | Histidine | 470 |
| TOM 30 | Arginine | 200 | 25 | Kolliphor ELP | 0.1 | Glutathione | 0.75 | Histidine | 470 |
| TOM 31 | Arginine | 50 | 100 | Kolliphor ELP | 0.1 | Glutathione | 0.75 | TRIS | 340 |
| TOM 33 | Mannitol | 50 | 25 | Kollidon 12PF | 0.1 | Glutathione | 0.075 | TRIS | 140 |
| TOM 34 | Arginine | 50 | 25 | Kolliphor ELP | 1 | Glutathione | 0.075 | Histidine | 170 |
| TOM 35 | Mannitol | 50 | 25 | Tween 80 | 1 | Glutathione | 0.75 | Histidine | 120 |
| TOM 36 | Arginine | 200 | 100 | Tween 80 | 1 | Glutathione | 0.75 | Histidine | 620 |
| TOM 37 | Arginine | 50 | 25 | Tween 80 | 0.1 | Glutathione | 0.075 | Histidine | 170 |

Example 3—1-Year Stability

The 1-year stability was assessed for the lead formulation. Various criteria have been monitored including pH, protein content (assessed by optical density), HMW species (assessed by SE-HPLC) and main peak (assessed by IEX-HPLC). The results are shown in Table 5 below, confirming stability of the lead formulation over at least one year.

TABLE 5

1-year stability data.

|  | T0 | 4 wk | 8 wk | 13 wk | 26 wk | 39 wk | 52 wk |
|---|---|---|---|---|---|---|---|
| pH | 6.0 | 6.0 | 6.0 | 6.0 | 6.0 | 6.0 | 6.0 |
| Protein content (mg/mL) | 181.7 | 181.5 | 183.0 | 184.2 | 184.0 | 180.0 | 179.5 |
| HMW (%) | 1.0 | 0.8 | 0.6 | 0.7 | 0.8 | 1.0 | 1.0 |
| Main peak (%) | 55.5 | 54.1 | 55.0 | 56.9 | 57.3 | — | — |

Wk = weeks

Abbreviations

DoE Design of experiment
DP Drug product
DS Drug substance
DSF Differential scanning fluorimetry
OD Optical density
PES Polyethersulphone
rpm rounds per minute
RT Room Temperature
SE-HPLC Size exclusion high performance liquid chromatography
HMW Hight Molecular Weight

REFERENCES

1) WO03/068260
2) WO2009/084659.
3) WO0213860
4) WO2011085158
5) WO2013063510.
6) High throughput thermostability screening of monoclonal antibody formulations. J Pharm Sci. 2010 April; 99(4): 1707-20

The invention claimed is:

1. A liquid pharmaceutical composition comprising:
   (a) an anti-IL-6 receptor (anti-IL-6R) antibody;
   (b) an histidine buffer;
   (c) a polyol;
   (d) 0.4 to 0.6 mM methionine;
   (e) a surfactant;
   (f) water for injection; and
   (g) optionally a salt.
   wherein the composition has a pH between 5.5 and 7.5;
   wherein the anti-IL6R antibody is selected from the group consisting of tocilizumab, sapelizumab, vobarilizumab or sarilumab.

2. The liquid pharmaceutical according to claim 1, wherein the composition has a pH between 6.0 and 6.5.

3. The liquid pharmaceutical composition according to claim 1, wherein the polyol is mannitol.

4. The liquid pharmaceutical composition according to claim 1, wherein the surfactant is a polysorbate.

5. The liquid pharmaceutical composition as claimed in claim 4, wherein the polysorbate is polysorbate 80.

6. The liquid pharmaceutical composition according to claim 1, wherein the optional salt is sodium chloride.

7. The liquid pharmaceutical composition according to claim 1, wherein the anti-IL6R antibody is tocilizumab.

8. The liquid pharmaceutical composition according to claim 1, wherein the composition comprises:
   15 to 200 mg/ml the anti-IL-6R antibody;
   10 to 25 mM histidine (or histidine buffer system);
   190 to 210 mM mannitol;
   0.4 to 0.6 mM methionine;
   0.4 to 0.9 mM polysorbate 80;
   water (for injection);
   75 to 125 mM sodium chloride.

9. A drug delivery device comprising a liquid pharmaceutical composition as claimed in claim 1.

10. A kit comprising: (i) the liquid pharmaceutical composition claim 1 and (ii) a drug delivery device; wherein the liquid pharmaceutical composition is optionally contained in a separate package or container from the drug delivery device;
    optionally wherein the kit further comprises a set of instructions regarding the administration of the liquid pharmaceutical composition.

11. A method of manufacturing the liquid pharmaceutical composition of claim 1, comprising mixing together the anti-IL-6R antibody, histidine buffer, polyol, methionine, and surfactant, and optionally the salt.

12. A method of treatment comprising administering a therapeutically effective amount of the liquid pharmaceutical composition of claim 1 to a subject having rheumatoid arthritis, juvenile idiopathic arthritis, Giant cell arteritis or systemic sclerosis.

* * * * *

SEQUENCE LISTING

<160> NUMBER OF SEQ ID NOS: 7

<210> SEQ ID NO 1
<211> LENGTH: 107
<212> TYPE: PRT
<213> ORGANISM: Artificial sequence
<220> FEATURE:
<223> OTHER INFORMATION: Light chain tocilizumab

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys
            100                 105

<210> SEQ ID NO 2
<211> LENGTH: 119
<212> TYPE: PRT
<213> ORGANISM: Artificial sequence
<220> FEATURE:
<223> OTHER INFORMATION: Heavy chain tocilizumab
<220> FEATURE:
<221> NAME/KEY: misc_feature
<222> LOCATION: (1)..(1)
<223> OTHER INFORMATION: Xaa can be any naturally occurring amino acid

<400> SEQUENCE: 2

Xaa Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
        115

<210> SEQ ID NO 3
<211> LENGTH: 107
<212> TYPE: PRT
<213> ORGANISM: Artificial sequence
<220> FEATURE:
<223> OTHER INFORMATION: Light chain sapelizumab

<400> SEQUENCE: 3

Asp Ile Gln Met Thr Gln Ser Pro Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
            100                 105

<210> SEQ ID NO 4
<211> LENGTH: 119
<212> TYPE: PRT
<213> ORGANISM: Artificial sequence
<220> FEATURE:
<223> OTHER INFORMATION: Heavy chain sapelizumab

<400> SEQUENCE: 4

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser
        115

<210> SEQ ID NO 5
<211> LENGTH: 245
<212> TYPE: PRT
<213> ORGANISM: Artificial sequence
<220> FEATURE:
<223> OTHER INFORMATION: Vobarilizumab

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
50                  55                  60

```
Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Gly Gly Gly Ser Gly Gly
            115                 120                 125         Gly

Gly Ser Glu Val Gln Leu Val Glu Ser Gly Gly Gly Leu Val Gln Pro
        130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
                180                 185                 190

Ser Val Lys Gly Arg Phe Thr Ile Ser Arg Asp Asn Ala Lys Thr Thr
            195                 200                 205

Leu Tyr Leu Gln Met Asn Ser Leu Arg Pro Glu Asp Thr Ala Val Tyr
        210                 215                 220

Tyr Cys Thr Ile Gly Gly Ser Leu Ser Arg Ser Ser Gln Gly Thr Leu
225                 230                 235                 240

Val Thr Val Ser Ser
                245

<210> SEQ ID NO 6
<211> LENGTH: 107
<212> TYPE: PRT
<213> ORGANISM: Artificial sequence
<220> FEATURE:
<223> OTHER INFORMATION: Light chain sarilumab

<400> SEQUENCE: 6

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Gly Lys Ala Pro Lys Leu Leu Ile
             35                  40                  45

Tyr Gly Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Ser Tyr Tyr Cys Gln Gln Ala Asn Ser Phe Pro Tyr
                 85                  90                  95

Thr Phe Gly Gln Gly Thr Lys Leu Glu Ile Lys
            100                 105

<210> SEQ ID NO 7
<211> LENGTH: 116
<212> TYPE: PRT
<213> ORGANISM: Artificial sequence
<220> FEATURE:
<223> OTHER INFORMATION: Heavy chain sarilumab

<400> SEQUENCE: 7

Glu Val Gln Leu Val Glu Ser Gly Gly Gly Leu Val Gln Pro Gly Arg
  1               5                  10                  15
```

```
Ser Leu Arg Leu Ser Cys Ala Ala Ser Arg Phe Thr Phe Asp Asp Tyr
            20              25              30

Ala Met His Trp Val Arg Gln Ala Pro Gly Lys Gly Leu Glu Trp Val
        35              40              45

Ser Gly Ile Ser Trp Asn Ser Gly Arg Ile Gly Tyr Ala Asp Ser Val
    50              55              60

Lys Gly Arg Phe Thr Ile Ser Arg Asp Asn Ala Glu Asn Ser Leu Phe
65              70              75              80

Leu Gln Met Asn Gly Leu Arg Ala Glu Asp Thr Ala Leu Tyr Tyr Cys
            85              90              95

Ala Lys Gly Arg Asp Ser Phe Asp Ile Trp Gly Gln Gly Thr Met Val
            100             105             110

Thr Val Ser Ser
        115
```